(12) United States Patent
Tsuruda et al.

(10) Patent No.: US 7,250,546 B2
(45) Date of Patent: Jul. 31, 2007

(54) ADHESIVE PREPARATIONS

(75) Inventors: Kiyomi Tsuruda, Saga (JP); Yasuhiro Ikeura, Saga (JP)

(73) Assignee: Hisamitsu Pharmaceuticals Co., Inc., Saga (JP)

( * ) Notice: Subject to any disclaimer, the term of this patent is extended or adjusted under 35 U.S.C. 154(b) by 0 days.

(21) Appl. No.: 11/634,481

(22) Filed: Dec. 5, 2006

(65) Prior Publication Data

US 2007/0083139 A1  Apr. 12, 2007

Related U.S. Application Data

(63) Continuation of application No. 10/149,942, filed as application No. PCT/JP00/08893 on Dec. 15, 2000, now abandoned.

(30) Foreign Application Priority Data

Dec. 15, 1999  (JP)  .................. 11-356482

(51) Int. Cl.
 *A61F 13/00* (2006.01)
 *A61F 13/02* (2006.01)
 *A61K 9/70* (2006.01)

(52) U.S. Cl. ........................... 602/48; 602/41; 602/52; 602/54; 424/443; 424/448; 424/449

(58) Field of Classification Search ............ 602/41–43, 602/48, 57, 52, 54; 424/443–448; 604/304–308
See application file for complete search history.

(56) References Cited

U.S. PATENT DOCUMENTS

| 4,776,850 | A | 10/1988 | Guse et al. |
| 5,770,221 | A | 6/1998 | Nakamura et al. |
| 2003/0138479 | A1 | 7/2003 | Mizota et al. |
| 2003/0149383 | A1 | 8/2003 | Ikeura et al. |
| 2003/0149385 | A1 | 8/2003 | Tsuruda et al. |
| 2004/0096491 | A1 | 5/2004 | Tateishi et al. |

FOREIGN PATENT DOCUMENTS

| EP | 374 980 | 6/1990 |
| JP | 11 152222 | 6/1999 |
| WO | WO-95/31190 | 11/1995 |

*Primary Examiner*—Kim M. Lewis
(74) *Attorney, Agent, or Firm*—Peter F. Corless; Christine C. O'Day; Edwards Angell Palmer & Dodge LLP

(57) ABSTRACT

This invention provides a patch with less skin stimulation, excellent in long time store stability and heat stability and having favorable tack during use. The patch comprising a styrene-isoprene-styrene block copolymer, polyisobutylene, tackifier, plasticizer and pharmaceutically effective ingredient, in which two or more kinds of polyisobutylene of different average molecular weight are used in combination and the viscosity of the adhesive of the patch is between 1500 and 30,000 poise (at 60° C.) and the tack of the patch is from 5 to 200 g/10 mm.

5 Claims, No Drawings

ADHESIVE PREPARATIONS

The present application is a Continuation application of U.S. Ser. No. 10/149,942, filed Jun. 14, 2002, now abandoned which in turn claimed the prior benefit of International Application No. PCT/JP00/08893, filed Dec. 15, 2000.

TECHNICAL FIELD

This invention concerns a patch applied to skins. More specifically, it relates to a patch giving less physical stimulations upon peeling such as pulling to hairs or skins and having good tack during use.

BACKGROUND OF THE INVENTION

For patches applied to skins, various patches or sticking plasters incorporating anti-inflammatory/analgesic agents such as methyl salicylate or L-menthol into a plaster layer have been developed and marketed as typical products. Usually, such patches or sticking plaster agents are prepared by forming an adhesive on a support made of films, non-woven fabrics or woven fabrics and have been used with an aim of protecting skins after suture and for anti-inflammatory and analgesic purpose to inflammation of shoulders, elbows, knees and waists.

To directly apply the patches or sticking plaster agents to skins, an appropriate tack is required so as to avoid peeling but it has been generally known that the tack inevitably causes damages to keratin layers when peeling from skins thereby causing skin eruptions or increase undesirable stimulations owing to from the ingredients of the base agent.

For overcoming the foregoing drawbacks, Japanese Patent Laid-Open No. 225314/1988, for instance, discloses a topical patch or sticking plaster agent formed by blending a water absorptive polymer to absorb and adsorb sweats or secretions discharged from skins thereby mitigating steaming or skin eruptions.

Further, Japanese Patent Laid-Open No. 157423/1995 discloses a percutanous patch or sticking plaster agent with an aim of mitigating skin stimulations by setting the tack, thickness and moisture permeability of the patch or sticking plaster agent each within a specified range.

However, during sticking although such formulations are effective to stimulants contained in secretions or sweats discharged from skins, they can not be said effective to physical stimulations upon peeling such as pulling hairs or skins, or favorable in view of upon appending.

DISCLOSURE OF THE INVENTION

This invention has been achieved for saving the problems in the patch or sticking plaster agent described above and intends to provide a patch with less stimulations to skins, excellent in long time store stability and heat stability, and having good tack during use.

The present inventors have made earnest studies for attaining the foregoing purpose and have accomplished this invention based on the finding that physical stimulations upon peeling such as pulling hairs or skins can be moderated and damages to skins can be suppressed effectively and excellent long time stability is obtainable by blending two or more of poly isobutylenes of different average molecular weight to an adhesive containing a styrene-isoprene-styrene block copolymer, a tackifier, a plasticizer and a pharmaceutically effective ingredient in ingredients of a base agent and defining the viscosity of the adhesive of the patch to 1,500-30,000 poise (at 60° C.) and the tack of the patch to 5-200 g/10 mm.

The patch according to this invention has the following constitution for attaining the purpose.

That is, this invention concerns a patch comprising a styrene-isoprene-styrene block copolymer, polyisobuytylene, a tackifier, a plasticizer and a pharmaceutical ingredient in which two or more of polyisobutylenes of different average molecular weight are used in combination, the viscosity of the adhesive of the patch is between 1,500 and 30,000 poise (at 60° C.) and the tack of the patch is from 5 to 200 g/10 mm.

More specifically, this invention has a feature in that the styrene-isoprene-styrene block copolymer has a weight average molecular weight of 100,000 to 300,000 with the blending amount thereof being from 10 to 40% by mass and that at least two kinds of the polyisobutylene having different viscosity average molecular weight are blended, one having a viscosity average molecular weight from 5,000 to 15,000 with the blending amount thereof being from 1 to 20% by mass and other having a viscosity average molecular weight of 50,000 to 200,000 with the blending amount thereof being from 0.2 to 15% by mass.

Further, this invention has a feature in blending a tackifier having a softening point of from 60° C. to 150° C. and the blending amount thereof from 5 to 50% by mass. Further, it has a feature in blending a plasticizer with a viscosity of from 10 to 100 centistokes (at 40° C.) and with a blending amount thereof from 10 to 70% by mass.

Further, this invention has a feature in blending a pharmaceutically effective ingredients with the blending amount thereof from 0.001 to 30% by mass.

In the patch of this invention, known fillers, softeners, anti-oxidant, UV-ray absorbent, perfuming agents and solubilizers can be blended as necessary.

BEST MODE FOR CARRYING THE INVENTION

The styrene-isoprene-styrene block copolymer in this invention preferably has a weight average molecular weight of 100,000 to 300,000 and can include, for example, KRATON D-KX401CS or D-1107CU (manufactured by Shell Chemical Co. Ltd.), SIS-5000 or SIS-5002 (manufactured by Japan Synthetic Rubber Co. Ltd.), Quintack 3530, 3421 or 3570C (manufactured by Nippon Zeon Co. Ltd.) and Solprene 428 (manufactured by Phillip Petroleum Co. Ltd). One or more of them can be blended in the styrene-isoprene-styrene block copolymer of this invention. The blending amount is within a range from 10 to 50% by mass, preferably, from 13 to 40% by mass and, more preferably, from 15 to 30% by mass.

Adhesion to skins, pains upon peeling and skin eruptions are greatly improved by using the styrene-isoprene-styrene block copolymer of this invention having the weight average molecular weight described above and at the blending ratio described above and, further preferably, by controlling the viscosity and the tack. If the blending amount is less than 10% by mass, it is not preferred since the cohesion or the shape retainability is reduced. Further, if the blending amount is 50% by mass or more, the cohesion of the base agent increases to undesirably lower the tack, make the plaster not uniform and deteriorate the operationability.

One of the features of this invention resides in the use of two or more kinds of polyisobutylene of different average molecular weight in combination and a combination of a polyisobutylene having a viscosity average molecular weight (according to Staudinger method) of 5,000 to 15,000 and a polyisobutylene having a viscosity average molecular weight of 50,000 to 200,000 is preferred and it is further preferred to blend the polyisobutylenes described above each at the specified blending amount.

Polyisobutylene having a viscosity average molecular weight from 5,000 to 15,000 can include, for example, Vistanex LM-MS, LM-MH (manufactured by Exxon Chemical Co. Ltd.), Tetrax 4T, 5T and 6T (manufactured by Nippon Petrochemical Co. Ltd.), Opanol B12SF and B15SF (manufactured by BASF Japan Co. Ltd.), and one or more of them can be blended. The blending amount is from 1 to 20% by mass, preferably, 2 to 18% by mass and, more preferably, 4 to 15% by mass. When the blending amount is less than 1% by mass, it is not preferred since the tack is insufficient. Further, if the blending amount is 20% by mass or more, cohesion or shape retainability are undesirably deteriorated.

Polyisobutylene having a viscosity average molecular weight of from 50,000 to 200,000 can include, for example, Vistanex MML-80, MML-100, MML-120 and MML-140 (manufactured by Exxon Chemical Co. Ltd.), Opanol B80, B100, B120 and B150 (manufactured by BASF Japan Co. Ltd.), and one or more of them can be blended. The blending amount is from 0.1 to 20% by mass, preferably, 1 to 18% by mass and, more preferably, 3.6 to 10% by mass. Viscosity adhesion to skins for a long time, pains upon peeling and skin eruptions are greatly improved by using the styrene-isoprene-styrene block copolymer of this invention having the weight average molecular weight described above at the blending ratio described above and, further preferably, by controlling the viscosity and the tack. If the blending amount is less than 0.1% by mass, it is not preferred since the cohesion and the shape retainability are reduced. Further, if the blending amount is 20% by mass or more, the cohesion of the base agent increases to undesirably lower the tack, make the plaster not uniform and deteriorate the operationability.

Further, in the patch of present invention, the viscosity of the adhesive used therefor is from 1500 to 30,000 poise (at 60° C.), the tack of the patch is from 5 to 200 g/10 mm, the viscosity of the adhesive is, preferably, from 2,000 to 20,000 poise (at 60° C.), and the tack of the patch is from 20 to 150 g/10 mm. Moreover, a preferable patch of the present invention has a ratio of the value i.e. viscosity (poise (at 60° C.)) divided by tack strength (g/10 mm) (viscosity/tack strength) of preferably 10-200, more preferably 30-150. In other words, the viscosity value (poise (at 60° C.)) of the present invention is 10-200, preferably 30-150 times as high as the tack strength (g/10 mm). According to the said ratios, it can be said that the present invention further relates to the patch comprising a styrene-isoprene-styrene block copolymer, a polyisobutylene, a tackifier, a plasticizer and a pharmaceutical ingredient, characterized by having a viscosity of 1,500-30,000 poise (60° C.) and an adhesive strength of 5-200 g/10 mm with the viscosity value (poise (at 60° C.)) being 10-200 times as high as the tack strength (g/10 mm). It is possible to suppress the tack for a long time on skins, pains upon peeling, skin eruptions and damages to keratin layers by using the patch showing such physical properties. If they are out of the range of the physical property values described above, they are not preferred in view of the tack to the bent portion, pains upon peeling, damages to keratin layers, skin eruptions and sliminess.

The adhesive according to this invention is an adhesive component comprising a styrene-isoprene-styrene block copolymer, polyisobutylene, a tackifier and a plasticizer and, after controlling the blending amount of the styrene-isoprene-styrene block copolymer, polyisobutylene and the tackifier, it can be controlled so as to provide the viscosity described above by a plasticizer.

The tack of the patch according to this invention is the tack of the patch which can be controlled mainly by controlling the composition of the adhesive.

Accordingly, the feature of the patch of this invention is to control the blending amount of the adhesive ingredient to the viscosity and the tack described above.

The tackifier preferably has the softening point of 60° C. to 150° C. and, for example, rosin ester, hydrogenated rosin ester, maleic acid modified rosin ester, polyterpen resin and petroleum resin can be used therefor and they can include, for example, Ester gum A, AA-G, H or HP (manufactured by Arakawa Chemical Co. Ltd.), Hariester L, S or P (manufactured by Harima Chemical Inc.), Pinecrystal KE-100 or KE-311 (manufactured by Arakawa Chemical Co. Ltd.), Hercolin D (manufactured by Rika Hercules Co. Ltd.), Foral 85 or 105 (manufactured by Rika Hercules Co. Ltd.), Stebelite ester 7 or 10 (manufactured by Rika Hercules Co. Ltd.), Pentalin 4820 or 4740 (manufactured by Rika Hercules Co. Ltd.), Arkon P-85 or P-100 (manufactured by Arakawa Kagaku Co. Ltd.), Escholetz 5300 (manufactured by Exxon Chemical Co. Ltd.), Clieron K, M or P (manufactured by Yasuhara Chemical Co. Ltd.) and one or more of them can be blended. The blending amount is from 5 to 50% by mass, preferably, 7 to 45% by mass and, more preferably, 10 to 40% by mass. They are formulated such that the viscosity and each the tack are within the range as described above. With this blending ratio, tack, adhesion to skin, pains upon peeling and skin eruptions of skins can be improved greatly. If the blending amount is less than 5% by mass, it is not preferred since the tack and the deposition to the skin are lowered. Further, if it is 50% by mass or more, it is not preferred since this lowers the shape retainability, and increases pains upon peeling, damages to keratin layers, skin eruptions and sliminess.

The plasticizer having a solution viscosity of from 10 to 100 centistoke (at 40° C.) is preferred and it can include, for example, almond oil, olive oil, camellia oil, persic oil, peanut oil, olefinic acid and liquid paraffin, and one or more of them can be blended. The blending ratio is from 10 to 70% by mass, preferably, 15 to 60% by mass, more preferably, 20 to 55% by mass and they are formulated such that the viscosity and the tack are each within the range described above. With this blending ratio, tack, adhesion to skins, dispersibility of chemicals in the base agent, pains upon peeling, damages to keratin layers, skin eruptions, and heat stability are greatly improved. When the blending amount thereof is less than 10% by mass, it is not preferred since the tack, adhesion to the skins and dispersibility of chemical are lowered and the viscosity of the patch is increased to undesirably make the patch not uniform and lower the operationability. Further, when it is 70% by mass or more, it is not preferred since this lowers the percutaneous absorption of chemicals and the shape retainability, and increases pains upon peeling, damages to keratin layers, skin eruptions and sliminess.

One or more of pharmaceutically effective ingredients can be blended being selected, for example, from skin stimulating agents such as L-menthol, camphor, menthe oil, capsicum extract, capsicine, benzyl nicotinate, salicylate, glycol salicylate, analgesic and anti-inflammatory agents such as ibuprofen, piroxicam, ketoprofen, indomethacin, suprofen, loxoprofen, dichlofenac sodium, flurbiprofen, felbinac, ketrolac, narcotic analgesic agent such as fentanyl citrate and morphine hydrochloride, non-narcotic analgesic agent such as pentazocine, butorphanol tartarate, buprenorphin hydrochloride and eptazocine hydrobromide, dysuria remedy such as oxybutynine hydrochloride, antifungal agent such as clotrimazole, bifonazole, miconazole nitrate, butenafine hydrochloride, tioconazole, lanoconazole, amorolfine hydrochloride and neticonazole hydrochloride. adrenocortical hormons such as hydrocortisone butyrate, dexamethasone, dexamethasone butyrate, betamethasone, betamethasone valerate, deprodone propionate, prednisolone, fluocinonide and fluocinolone acetonide, local anesthetics such as ethyl aminobenzoate, tetracaine hydrochloride, procaine hydrochloride, lidocain hydrochloride, β-blocking agents such as propranolol hydrochloride, pindolol, cateolol hydrochloride, thymolol maleate, coronary dilator such as nitroglyceline, isosorbide nitrate, niphedipine, diltiazem hydrochloride, dipyridamole, antihistamic agents such as diphenhydramine hydrochloride, chlorophenylamine maleate and cresol hydrochloride, antitussive and expectorants or anti-allergic agents such as salbutamol sulfate, procatechol hydrochloride, sodium chromoglycate, tranirust, ketothiophene and azerastine, bronchial asthma curing drugs such as procatechol, isoproterelol hydrochloride and theophylline, as well as prostaglandins, hormons, crude drug extracts and vitamins. The blending ratio is from 0.001 to 30% by mass, preferably, 0.01 to 16% by mass and they also includes pharmaceutically acceptable forms of inorganic or organic salts and sufficient pharmaceutical effect can be expected by the blending ratio. When the blending ratio is less than 0.001% by mass, no sufficient pharmaceutical effect can be provided and, when it is 30% by mass or more, it is not preferred since this causes skin eruptions with pharmaceutically effective ingredients, degrades the shape retainability of the adhesive layer and increases sliminess.

The support in this invention is not particularly restricted and the material is selected from films, woven fabrics or non-woven fabrics, for example, of polyethylene, polypropylene, polybutadiene, polyester, nylon and polyurethane.

Among them, polyester non-woven fabrics are used preferably since they have favorable feelings upon touch and use. Further, the basis weight (weight per unit area) of the supports is preferably from 70 to 130 g/cm² and the thickness thereof is preferably from 0.1 to 2 mm. If the basis weight or the thickness of the support is less than the lower limit described above, the patch (laminate) tends to be creased or entangled upon appending operation failing to obtain good feeling upon use. On the other hand, if it exceeds the upper limit, the patch (laminate) lacks in softness and flexibility tending to cause a sense of incongruity such as cramp upon appending.

The load on 50% elongation of the stretchable support used in this invention is preferably from 0.98 to 14.71 N/5 cm both in the directions of the longer side and the shorter side and, more preferably, from 1.96 to 9.81 N/5 cm in the direction of the longer side and from 0.98 to 9.81 N/5 cm in the direction of the shorter side. When the load on 50% elongation of the support is less than the lower limit, the laminate loses so-called stiffness, so that the patch can no more be supported firmly tending to cause a difficulty in obtaining favorable feeling upon use in the appending operation. On the other hand, when the load upon 50% elongation of the support exceeds the upper limit, conformity with skins becomes insufficient and it tends to be peeled easily even by slight movement in a case of appending to joints such as elbow or knee. The load at the time of 50% elongation used herein refers to the value measured according to the method in the item "Load for Stretching" in JIS General Fabric Test Method L1096 provided that the 80% of the elongation at the time of loading 1.5 kgf is replaced by 50% of the distance between the gripping portions. Thus, the load at the time of 50% elongation according to the present invention refers to the force per unit width [5N/cm] when a test piece of 30 cm long and 5 cm wide is pulled in each of the long side and short side directions at tensile rate of 200 mm/min with a distance between the gripping portions of 20 cm by the use of a tensile test machine as defined in JIS Z 0237 and has reached 50% elongation along the test side on the basis of the distance between the gripping portions (it means that the distance between the gripping portions along the test side has become 30 cm).

Further, recovery rate upon 50% elongation of the stretchable support used in this invention is preferably from 50 to 95% and, more preferably, from 50 to 95% in the direction of the longer side and from 60 to 90% in the direction of the shorter side. When the recovery rate upon 50% elongation of the laminate is less than the lower limit, conformity with skins becomes insufficient and it tends to be peeled even for a slight movement in a case of appending to joints such as elbow or knee. On the other hand, conformity with skins is improved as the recovery rate upon 50% elongation of the laminate increases but, when it exceeds the upper limit, the patch (laminate) tends to be creased or entangled upon appending operation tending to cause a difficulty in obtaining favorable feeling in use. The recovering rate at 50% elongation herein refers to the value measured according to Method A (Repeated constant elongation at constant speed method) of "Elongation Recovering Rate and Residual Strain Rate" in JIS General Fabric Test Method L1096 provided that the 80% of the elongation at the time of loading 1.5 kgf is replaced by 50% of the distance between the grip sections. Thus, the recovering rate at 50% elongation according to the present invention refers to the value [%] obtained by 1) stretching a test specimen of 30 cm long and 5 cm wide in each of the long side and short side directions at tensile rate of 200 mm/min with a distance between the gripping portions of 20 cm by the use of a tensile test machine as defined in JIS Z 0237 until the piece reaches 50% elongation along the test side based on the distance between the gripping portions (it means that the distance between the gripping portions along the test sides has become 30 cm), followed by allowing it to leave for 1 minute, 2) releasing the test specimen back to the original position at a rate of 200 mm/min and allowing it to leave for 3 minutes, 3) repeating both the steps 5 times, 4) subtracting the length to the first loading point (residual strain) from the length of the gripping portions when further stretching the piece at a rate of 200 mm/min, and dividing the difference with said length of the gripping portions.

In the patch according to this invention, known other additives can further be blended. There can be blended optionally, for example, fillers such as zinc oxide, aluminum oxide, titanium dioxide, calcium carbonate, synthesis aluminum silicate, silicas and magnesium oxide, anti-oxidizing agents such as ascorbic acid, tocopherol acetate, natural vitamin E, dibutylhydroxytoluene, propyl gallate, UV-ray absorbents such as 2-hydroxy-4-methoxy benzophenone, glycol salicylate and 2-(2-hydroxy-5-methylphenyl) benzotriazole, perfuming agents or solubilizing agents such as oleic acid, glycol salicylate, benzyl alcohol, isopropyl myristate, crotamitone, oleyl alcohol, mentha oil, blue gum oil, limonen, isopregole or like other essential oils, or surface active agents known so far.

Then, method of preparing the patch according to this invention is to be explained. First, a tackifier and a plasticizer are added to a styrene-isoprene-styrene block copolymer and polyisobutylene to adjust the viscosity and the tack, a filler and an anti-oxidant agent are optionally added at a predetermined ratio to make a mixture, which is stirred under heating in a nitrogen gas atmosphere to form a solubilized product. The temperature for stirring is of from 110 to 200° C. and stirring time is between 30 to 120 min. Then, a pharmaceutically effective ingredient is added within a range of temperature upon stirring from 110 to 200° C. for the solubilized product and mixed for 1 to 30 min to obtain a homogeneous solubilized product. Then, the solubilized product is directly cast on a support by a usual method and then covered with a releasable cover, or it may be cast once on a releasable cover and then transferred under pressure covering the support. The releasable cover can be selected properly from release paper, cellophane or film of polyethylene, polypropylene, polyester applied with releasing treatment.

The order of blending each of the raw materials, the pharmaceutically effective ingredient and other ingredients in the preparation method described above is merely an example thereof and this invention is not limited to such blending sequence.

When the styrene-isoprene-styrene block copolymer and two or more kinds of polyisobutylene of different average molecular weight are used in combination and adjusted to the specified viscosity and the tack described above, the patch according to this invention having the following excellent features can be provided when based only on the ingredients, as well as the tackifier, plasticizer and pharmaceutically effective ingredient as the main agent.

(1) Pains upon peeling can be moderated remarkably.
(2) Damages to keratin layers are remarkably moderated
(3) It is highly safe to skins and can be applied directly to a human body
(4) Adhesion (tack) and cohesion are excellent.
(5) Favorable shape retainability and it is not subject to thermal deformation.

EXAMPLES

Then, examples of the patch according to this invention are to be shown but they are not always restricted to the following formulations. "%" means "% by mass".

Example 1

| | |
|---|---|
| Styrene-isoprene-styrene block copolymer (KRATON D-1107CU) | 22.0% |
| Polyisobutylene (Tetrax 6T) | 15.0% |
| Polyisobutylene (Opanol B80) | 7.0% |
| Hydrogenated rosin ester (Stebelite ester 7) | 12.0% |
| Liquid paraffin (Cristol J-352) | 40.0% |
| Dibutylhydroxytoluene | 1.0% |
| Felbinac | 3.0% |

Patch was obtained based on the formulation in accordance with the preparation method described above and by cutting into a desired size. Stretchable woven fabrics made of a polyester material was used as a support.

Example 2

| | |
|---|---|
| Styrene-isoprene-styrene block copolymer (KRATON D-KX401CS) | 16.0% |
| Polyisobutylene (Vistanex LM-MS) | 10.0% |
| Polyisobutylene (Vistanex MML-140) | 14.0% |
| Hydrogenated rosin ester (Foral 105)% | 18.0% |
| Liquid paraffin (Cristol J-352) | 37.0% |
| Ketoprofen | 4.0% |
| L-menthol | 1.0% |

Patch was obtained based on the formulation in accordance with the preparation method described above and by cutting into a desired size. Stretchable woven fabrics made of a polyester material was used as a support.

Example 3

| | |
|---|---|
| Styrene-isoprene-styrene block copolymer (KRATON D-1107CU) | 25.0% |
| Polyisobutylene (Tetrax 5T) | 3.0% |
| Polyisobutylene (Vistanex MML-140) | 1.0% |
| Hydrogenated rosin ester (Foral 85) | 10.0% |
| Liquid paraffin (Cristol J-352) | 50.0% |
| Indomethacine | 5.0% |
| Crotamiton | 6.0% |

Patch was obtained based on the formulation in accordance with the preparation method described above and by cutting into a desired size. Woven fabrics made of a polyester material was used as a support.

Example 4

| | |
|---|---|
| Styrene-isoprene-styrene block copolymer (KRATON D-1107CU) | 15.0% |
| Polyisobutylene (Vistanex LM-MH) | 13.0% |
| Polyisobutylene (Vistanex MML-100) | 13.0% |
| Maleic acid-modified rosin ester (Malkeed) | 13.0% |
| Liquid paraffin (Cristol J-352) | 35.0% |
| Glycol salicylate | 5.0% |
| L-menthol | 6.0% |

Patch was obtained based on the formulation in accordance with the preparation method described above and by cutting into a desired size. Woven fabrics made of a polyester material was used as a support.

Example 5

| | |
|---|---|
| Styrene-isopren-styrene block copolymer (SIS-5000) | 29.0% |
| Polyisobutylene (Opanol B15SF) | 16.0% |
| Polyisobutylene (Opanol B120) | 1.0% |
| Petroleum resin (Arkon P-85) | 18.0% |
| Liquid paraffin (Cristol J-352) | 23.0% |
| Titanium dioxide | 3.0% |
| Methyl salicylate | 5.0% |
| L-menthol | 5.0% |

Patch was obtained based on the formulation in accordance with the preparation method described above and by cutting into a desired size. Woven fabrics made of a polyester material was used as a support.

Example 6

| | |
|---|---|
| Styrene-isoprene-styrene block copolymer (SIS-5000) | 15.0% |
| Polyisobutylene (Opanol B15SF) | 5.0% |
| Polyisobutylene (Opanol B120) | 15.0% |
| Petroleum resin (Edcolets 5300) | 18.0% |
| Liquid paraffin (Cristol J-352) | 33.0% |
| Zinc oxide | 3.0% |
| Methyl salicylate | 8.0% |
| L-menthol | 3.0% |

Patch was obtained based on the formulation in accordance with the preparation method described above and by cutting into a desired size. Woven fabrics made of a polyester material was used as a support.

Example 7

| | |
|---|---|
| Styrene-isoprene-styrene block copolymer (D-KX401CS) | 23.0% |
| Polyisobutylene (Tetrax 6T) | 14.0% |
| Polyisobutylene (Vistanex MML-100) | 8.0% |
| Petroleum resin (Arkon P-100) | 15.0% |
| Liquid paraffin (Cristol J-352) | 24.0% |
| Glycol salicylate | 8.0% |
| L-menthol | 8.0% |

Patch was obtained based on the formulation in accordance with the preparation method described above and by cutting into a desired size. Woven fabrics made of a polyester material was used as a support.

Example 8

| | |
|---|---|
| Styrene-isoprene-styrene block copolymer (D-KX401CS) | 20.0% |
| Polyisobutylene (Tetrax 4T) | 17.0% |
| Polyisobutylene (Vistanex MML-140) | 6.0% |
| Polyterpene resin (Clieron K-100) | 14.0% |
| Liquid paraffin (Cristol J-352) | 30.0% |
| Glycol salicylate | 10.0% |
| L-menthol | 3.0% |

Patch was obtained based on the formulation in accordance with the preparation method described above and by cutting into a desired size. Woven fabrics made of a polyester material was used as a support.

Example 9

| | |
|---|---|
| Styrene-isoprene-styrene block copolymer (Quintack 3570C) | 17.0% |
| Polyisobutylene (Vistanex LM-MS) | 2.0% |
| Polyisobutylene (Opanol B150) | 1.0% |
| Hydrogenated rosin ester (Stebelite ester 7) | 28.0% |
| Liquid paraffin (Cristol J-352) | 41.0% |
| Glycol salicylate | 5.0% |
| L-menthol | 6.0% |

Patch was obtained based on the formulation in accordance with the preparation method described above and by cutting into a desired size. A film made of a vinyl chloride material was used as a support.

Example 10

| | |
|---|---|
| Styrene-isoprene-styrene block copolymer (KRATON D-1107CU) | 15.0% |
| Polyisobutylene (Tetrax 4T) | 10.0% |
| Polyisobutylene (Vistanex MML-120) | 17.0% |
| Petroleum resin (Arkon P-100) | 20.0% |
| Liquid paraffin (Cristol J-352) | 24.0% |
| Methyl salicylate | 8.0% |
| L-menthol | 6.0% |

Patch was obtained based on the formulation in accordance with the preparation method described above and by cutting into a desired size. A film made of a vinyl chloride material was used as a support.

Example 11

| | |
|---|---|
| Styrene-isoprene-styrene block copolymer (KRATON D-1107CU) | 22.0% |
| Polyisobutylene (Tetrax 5T) | 10.0% |
| Polyisobutylene (Vistanex MML-100) | 7.0% |
| Hydrogenated rosin ester (Foral 85) | 28.0% |
| Liquid paraffin (Cristol J-352) | 24.0% |
| Flurbiprofen | 4.0% |
| Crotamiton | 5.0% |

Patch was obtained based on the formulation in accordance with the preparation method described above and by cutting into a desired size. A film made of a vinyl chloride material was used as a support.

Example 12

| | |
|---|---|
| Styrene-isoprene-styrene block copolymer (KRATON D-1107CU) | 23.0% |
| Polyisobutylene (Tetrax 5T) | 8.0% |
| Polyisobutylene (Vistanex MML-100) | 8.0% |
| Hydrogenated rosin ester (Foral 85) | 26.0% |
| Liquid paraffin (Cristol J-352) | 34.99% |
| Betamethasone valerate | 0.01% |

Patch was obtained based on the formulation in accordance with the preparation method described above and by cutting into a desired size. A film made of a vinyl chloride material was used as a support.

Comparative Example 1

| | |
|---|---|
| Styrene-isoprene-styrene block copolymer (KRATON D-1107CU) | 18.0% |
| Polyisobutylene (Vistanex LM-MH) | 15.0% |
| Hydrogenated rosin ester (KE-311) | 14.0% |
| Liquid paraffin (Cristol J-352) | 48.0% |
| Ketoprofen | 2.0% |
| L-menthol | 3.0% |

Patch was obtained based on the formulation in accordance with the preparation method described above and by cutting into a desired size. A woven fabric made of a polyester material was used as a support.

Comparative Example 2

| | |
|---|---|
| Styrene-isoprene-styrene block copolymer (D-KX401CS) | 18.0% |
| Polyisobutylene (Vistanex MML-100) | 10.0% |
| Hydrogenated rosin ester (KE-311) | 14.0% |
| Liquid paraffin (Cristol J-352) | 49.0% |
| Indomethacin | 4.0% |
| Crotamiton | 5.0% |

Patch was obtained based on the formulation in accordance with the preparation method described above and by cutting into a desired size. A woven fabric made of a polyester material was used as a support.

Comparative Example 3

| | |
|---|---|
| Styrene-isoprene-styrene block copolymer (KRATON D-KX 401CS) | 28.0% |
| Hydrogenated rosin ester (KE-311) | 14.0% |
| Liquid paraffin (Cristol-352) | 48.0% |
| Glycol salicylate | 5.0% |
| L-menthol | 5.0% |

Patch was obtained based on the formulation in accordance with the preparation method described above and by cutting into a desired size. A woven fabric made of a polyester material was used as a support.

Comparative Example 4

| | |
|---|---|
| Styrene-isoprene-styrene block copolymer (KRATON D-1107CU) | 28.0% |
| Hydrogenated rosin ester (KE-311) | 42.0% |
| Liquid paraffin (Crystol J-352) | 20.0% |
| Glycol salicylate | 5.0% |
| L-menthol | 5.0% |

Patch was obtained based on the formulation in accordance with the preparation method described above and by cutting into a desired size. A woven fabric made of a polyester material was used as a support.

Comparative Example 5

| | |
|---|---|
| Styrene-isoprene-styrene block copolymer (SIS-5000) | 17.0% |
| Hydrogenated Rosin ester (Ester gum H) | 52.0% |
| Liquid paraffin (Cristol J-352) | 21.0% |
| Glycol salicylate | 5.0% |
| L-menthol | 5.0% |

Patch was obtained based on the formulation in accordance with the preparation method described above and by cutting into a desired size. A film fabric made of a vinyl chloride material was used as a support.

Comparative Example 6

| | |
|---|---|
| 2-ethylhexylester acrylate | 55.0% |
| Methoxyethyl acrylate | 26.0% |
| Vinyl acetate | 14.7% |
| Azobisisobutylonitrile | 0.3% |
| felbinac | 4.0% |

2-ethylhexyl acrylate, methoxyethyl acrylate, vinyl acetate and azobisisobutylonitrile were charged into a reaction vessel, polymerization was started while elevating the temperature to 65° C. in a nitrogen atmosphere, the reaction was continued for 10 hours while adding ethyl acetate dropwise so that the solid concentration was increased to 50%, while controlling the temperature, and further the reaction product was aged at 80° C. to obtain a copolymer solution. Felbinac was added and mixed with the obtained copolymer solution, the mixture was cast on a releasable coat and dried, coated with a vinyl chloride film, transferred under pressure, cut into a predetermined size to form a patch.

Test Example 1

(Tack Test)

A patch preliminarily left in a thermostable chamber at 25° C. for 30 min or more was prepared to a face of 20 mm width and about 100 mm length. It was mated at one end to a test board made of a phenol resin of 25 mm width and 50 mm length and left at 25° C. in a thermostable chamber for 30 min or more and appended rapidly by a width of 20 mm and a length of 50 mm in the same manner, a rubber roller of a weight of 800 g was passed twice over the product at a speed of 300 mm per one minute. Immediately, the free end of the product appended to the test board was turned back by 180° in the thermostable chamber at 25° C., and a non-shrinkable film of 20 mm width and about 100 mm length was appended to the adhesive surface. It was peeled continuously at a rate of 300 mm per 1 min using a tensile tester while having the free end to which the non-shrinkable film of the invention was appended was fastened strictly at the upper portion, and the test end was fastened at the lower end with retainers, and a load average value between 20 mm and 40 mm after the start of the test was measured. The results are shown in Table 1 (refer to: "Plaster" according to $13^{th}$ Revised Japan Pharmacopoeia, Para D-871).

Test Example 2

(Viscosity Test)

The viscosity of plasters was measured by a Shimazu flow tester manufactured by Shimazu Seisakusho Co. Ltd. About 2 g of plaster was filled in a cylinder having an area of 100 mm² and a height of 40 mm and previously kept at 60° C., and left for 5 min. A die having a fine tube of a diameter of 0.5 mm and a length of 1 mm was previously attached on the lower portion of the cylinder. After leaving it for 5 min, the surface of 100 mm² at the upper portion of the cylinder was pressed by a piston under a load of 10 kg. The flow rate of the plaster molten and extruded from the fine tube of the die at the lower portion of the cylinder was measured to obtain the viscosity of the plaster. The results are shown in Table 1 (refer to: Handling Manual for Shimazu flow tester CFT-100C, para 35).

TABLE 1

|  | Adhesion (g/10 mm) | Viscosity (poise) |
| --- | --- | --- |
| Example 1 | 42 | 3200 |
| Example 2 | 53 | 7540 |
| Example 3 | 36 | 4430 |
| Example 4 | 52 | 2520 |
| Example 5 | 61 | 2280 |
| Example 6 | 47 | 3350 |
| Example 7 | 62 | 4620 |
| Example 8 | 54 | 3250 |
| Example 9 | 123 | 8530 |
| Example 10 | 145 | 12830 |
| Example 11 | 135 | 18320 |
| Example 12 | 115 | 10560 |
| Comparative Example 1 | 5 | 1200 |
| Comparative Example 2 | 43 | 18890 |
| Comparative Example 3 | 33 | 132600 |
| Comparative Example 4 | 214 | 67530 |
| Comparative Example 5 | 204 | 75520 |
| Comparative Example 6 | 258 | 35210 |

Test Example 3

(Functional Patch Test)

For Examples 1 to 5, 9 to 10 and Comparative Examples 1 to 6, a functional patch test was conducted for 30 healthy adult men. The specimens were applied to their elbows for 6 hours at different days. The plasters were sized to a width of 70 mm and a length of 100 mm in any of the examples and the comparative examples. The results are shown in Table 2. The products according to the invention were superior to those of the comparative examples for both of adhesion and pains upon peeling.

TABLE 2

|  | Adhesion | | | Pain upon peeling | | |
| --- | --- | --- | --- | --- | --- | --- |
|  | Not peeled | Peeled at end portion | peeled by ¼ or more | No pain | Slight pain | Pain |
| Example 1 | 25 | 4 | 1 | 24 | 6 | 0 |
| Example 2 | 28 | 2 | 0 | 26 | 4 | 0 |
| Example 3 | 24 | 4 | 2 | 22 | 7 | 2 |
| Example 4 | 26 | 3 | 1 | 28 | 2 | 0 |
| Example 5 | 24 | 5 | 1 | 24 | 6 | 0 |
| Example 9 | 22 | 5 | 3 | 23 | 6 | 1 |
| Example 10 | 24 | 4 | 2 | 22 | 8 | 0 |
| Example 11 | 22 | 6 | 2 | 24 | 5 | 1 |
| Comparative Example 1 | 0 | 2 | 28 | 27 | 3 | 0 |
| Comparative Example 2 | 2 | 8 | 20 | 20 | 8 | 2 |
| Comparative Example 3 | 0 | 4 | 26 | 30 | 0 | 0 |
| Comparative Example 4 | 28 | 2 | 0 | 0 | 2 | 28 |
| Comparative Example 5 | 0 | 1 | 29 | 0 | 7 | 23 |
| Comparative Example 6 | 0 | 0 | 30 | 0 | 5 | 25 |

Test Example 4

(Keratin Peeling Amount Measuring Test)

Specimens each cut into 1 cm square for Examples 2, 4, 7 and 9 and Comparative Examples 4 and 5 were appended on forearms of healthy adult men for 30 min and evaluation was made based on the ratio of the adhesive area to which keratin was adhered relative to the area of the specimen when observed under an electron microscope. The results are shown in Table 3. The peeling amount of keratin was extremely smaller in those of this invention compared with comparative examples.

TABLE 3

|  | Keratin peeling area |
| --- | --- |
| Example 2 | 5% or less |
| Example 4 | 15% |
| Example 7 | 10% |
| Example 9 | 15% |
| Comp. Example 4 | 90% or more |
| Comp. Example 5 | 90% or more |
| Comp. Example 6 | 90% or more |

Test Example 5

(Skin Safety Test 1 (Healthy Person Patch Test))

For Examples 2 and 4 and Comparative Example 4, a 48 hour closed patch test was conducted at the inside of upper arms on 30 healthy adult men and the state of skins at the appended portion one hour and 24 hours after peeling was judged. The patch used in the test was a disc sized 2 cm in diameter. The results are shown in Table 4. Those of this invention were excellent in skin safety.

TABLE 4

| Lapse of time for peeling | | +++ | ++ | + | ± | − | Total | Positive rate |
|---|---|---|---|---|---|---|---|---|
| | | | Judgement | | | | | |
| 1 hour | Example 2 | — | — | — | 5 | 25 | 30 | 16.7 |
| | Example 4 | — | — | — | 5 | 25 | 30 | 16.7 |
| | Comp. Example 5 | — | — | — | 11 | 19 | 30 | 36.7 |
| | JP Plaster | — | — | — | 7 | 23 | 30 | 23.3 |
| 24 hour | Example 2 | — | — | — | 4 | 26 | 30 | 13.3 |
| | Example 4 | — | — | — | 6 | 24 | 30 | 20.0 |
| | Comp. Example 5 | — | — | — | 4 | 26 | 30 | 13.3 |
| | JP Plaster | — | — | — | 5 | 25 | 30 | 16.7 |

Criterion for plaster test judgement
−: no reaction
±: slight erythema
+: distinct erythema
++: erythema + papule or edema
+++: erythema + papule, edema + vesicle Test Example 6

(Heat Stability Test 1)

Stocking plaster agents each of 70 mm with and 100 mm length were prepared from Examples 1, 3, 4, 5, 6, 7, 8 and 12, and Comparative Examples 1, 2 and 3 and stored under sealing at 40° C. for 3 month in composite films mainly made of aluminum. After opening the seal, the tack test was conducted and evaluation was made based on the rate of reduction relative to the initial value. The results are shown in Table 5. Those of this invention showed less reduction of the tack relative to comparative examples.

TABLE 5

| | Reduction of rate of tack |
|---|---|
| Example 1 | 8% |
| Example 2 | 11% |
| Example 3 | 8% |
| Example 4 | 10% |
| Example 5 | 12% |
| Example 6 | 13% |
| Example 7 | 12% |
| Example 8 | 10% |
| Comp. Example 1 | 41% |
| Comp. Example 2 | 32% |
| Comp. Example 3 | 33% |
| Comp. Example 4 | 55% |

Test Example 7

(Heat Stabl Test 2)

Square shapes each in 3 cm×3 cm size were punched from the patches of Examples 9, 10, 11 and 12, and Comparative Examples 5 and 6 and stored under sealing at 60° C. for 3 months with a composite film mainly made of aluminum. After opening the seal, extruded width of the adhesive and the stickiness on the adhesive surface were observed. The results are shown in Table 6.

Those of this invention showed narrower extrusion width relative to comparative examples, no stickiness and excellent heat stability.

TABLE 6

| | Extrusion width | Stickiness | Evaluation |
|---|---|---|---|
| Example 9 | 0.5 mm or less | N | ○ |
| Example 10 | 0.5 mm or less | N | ○ |
| Example 11 | 0.5 mm or less | N | ○ |
| Example 12 | 0.5 mm or less | N | ○ |
| Comp. Example 5 | 2.0 mm | Y | X |
| Comp. Example 6 | 1.5 mm | Y | X |

INDUSTRIAL APPLICABILITY

Since the viscosity of the adhesive used for the patch and the tack in the patch according to this invention agent are defined each within the specified range, pains upon peeling are less, damages to the keratin layers are moderated remarkably, safety to skins is high, heat stability is excellent and, further, the tack is favorable, so that it can be utilized as various kinds of application uses of the medical patch, which are extremely useful industrially.

The invention claimed is:

1. A patch comprising an adhesive comprising a styrene-isoprene-styrene block copolymer, polyisobutylene, a tackifier, a plasticizer and a pharmaceutically effective ingredient in which 1-20% by mass of polyisobutylene having a viscosity average molecular weight of 5,000-15,000 and 0.1-20% by mass of polyisobutylene having a viscosity average molecular weight of 50,000-200,000 are blended, the viscosity of the of the adhesive of the patch is between 1500 and 30,000 poise (at 60° C.) and the tack of the patch is from 5 to 200 g/10 mm.

2. The patch as defined in claim 1, wherein the weight average molecular weight of the styrene-isoprene-styrene block copolymer is from 100,000 to 300,000 and the blending amount thereof is from 10 to 50% by mass.

3. The patch as defined in claim 1, wherein the softening point of the tackifier is from 60° C. to 150° C. and the blending amount thereof is from 5 to 50% by mass.

4. The patch as defined in claim 1, wherein the viscosity of the plasticizer is from 10 to 100 centistokes (at 40° C.) and the blending ratio thereof is from 10 to 70% by mass.

5. The patch as defined in claim 1, wherein the blending ratio of the pharmaceutically effective ingredient is from 0.001 to 30% by mass.

* * * * *